United States Patent [19]
Didierlaurent et al.

[11] Patent Number: 5,942,622
[45] Date of Patent: Aug. 24, 1999

[54] ACID PYRAZOLE DERIVATIVES, PREPARATION METHOD THEREFOR, USE THEREOF AS DRUGS, NOVEL USE THEREFOR, AND PHARMACEUTICAL COMPOSITIONS CONTAINING SUCH DERIVATIVES

[75] Inventors: Stanislas Didierlaurent, Lagny sur Marne; Michel Fortin; Jidong Zhang, both of Paris, all of France

[73] Assignee: Hoechst Marion Roussel, France

[21] Appl. No.: 09/043,094

[22] PCT Filed: Oct. 16, 1996

[86] PCT No.: PCT/FR96/01615

§ 371 Date: Apr. 22, 1998

§ 102(e) Date: Apr. 22, 1998

[87] PCT Pub. No.: WO97/15570

PCT Pub. Date: May 1, 1997

[30] Foreign Application Priority Data

Oct. 20, 1995 [FR] France .................. 95 12330

[51] Int. Cl.[6] ............. C07D 401/04; C07D 257/04; C07D 231/18
[52] U.S. Cl. ............ 546/275.4; 548/251; 548/374.1
[58] Field of Search ............. 548/374.1, 251; 546/275.4

[56] References Cited

FOREIGN PATENT DOCUMENTS

| | | |
|---|---|---|
| 0449699 | 10/1991 | European Pat. Off. . |
| 9402474 | 2/1994 | WIPO . |
| 96/12706 | 2/1996 | WIPO . |
| 9612706 | 5/1996 | WIPO . |

*Primary Examiner*—Johann Richter
*Assistant Examiner*—Dominic Keating
*Attorney, Agent, or Firm*—Bierman, Muserlian and Lucas

[57] ABSTRACT

The subject of the invention is the products of formula (I):

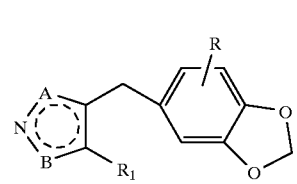

(I)

in which one of A and B represents a nitrogen atom and the other one of A and B represents a methine radical, such that:

A represents either nitrogen substituted in particular by alkyl, or methine substituted in particular by phenyl, thienyl or pyridyl, B represents either nitrogen substituted in particular by cyclohexylalkyl, or methine substituted in particular by alkylthio, $R_1$ represents in particular carboxy, R represents in particular halogen, as well as the isomers and salts of said products of formula(I).

6 Claims, No Drawings

ACID PYRAZOLE DERIVATIVES, PREPARATION METHOD THEREFOR, USE THEREOF AS DRUGS, NOVEL USE THEREFOR, AND PHARMACEUTICAL COMPOSITIONS CONTAINING SUCH DERIVATIVES

This application is a 371 of PCT/FR96/01615 filed Oct. 16, 1996.

The present invention relates to new derivatives of acid pyrazoles, their preparation process, the new intermediates obtained, their use as medicaments, the pharmaceutical compositions containing them and the new use of such derivatives of acid pyrazoles.

The subject of the present invention is the products of formula (I):

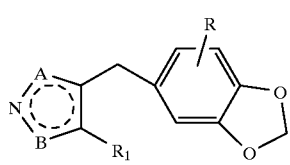

in which one of A and B represents a nitrogen atom and the other of A and B represents a methine radical, defined as follows:

A represent either a nitrogen atom substituted by ZNA which represents a linear or branched alkyl or alkenyl radical containing at most 10 carbon atoms, or a methine radical substituted by ZCA which represents a saturated or unsaturated cyclic radical constituted by 3 to 7 members, and optionally containing one or more identical or different heteroatoms chosen from oxygen, sulphur and nitrogen atoms, B represents either a nitrogen atom substituted by ZNB which represents a linear or branched alkyl or alkenyl radical containing at most 10 carbon atoms, optionally substituted by a cycloalkyl radical containing 5 or 6 members itself optionally substituted by a carboxy, alkyl, alkoxy, alkoxyalkyl, carboxyalkyl or carboxyalkoxyalkyl radical, containing at most 6 carbon atoms, or a methine radical substituted by ZCB which represents a linear or branched alkyl, alkenyl or alkylthio radical containing at most 10 carbon atoms, or a cycloalkylthio radical, containing 5 or 6 members, all of these radicals being optionally substituted by a carboxy or phenyl radical itself optionally substituted by a free or esterified carboxy radical, a linear or branched alkyl or alkoxy radical containing at most 4 carbon atoms, R represents a hydrogen or halogen atom, or a linear or branched alkoxy radical containing at most 4 carbon atoms, $R_1$ represents a free, salified or esterified carboxy radical or an acid isosteric function, the dotted lines indicate that the ring which carries A and B is unsaturated, said products of formula (I) being in all possible racemic, enantiomeric and diastereoisomeric isomer forms, as well as the addition salts with mineral and organic acids or with mineral and organic bases of said products of formula (I).

In the products of formula (I) and in what follows:

the term linear or branched alkyl radical designates the following radicals: methyl, ethyl, propyl, isopropyl, butyl, isobutyl, sec-butyl, tert-butyl, pentyl, isopentyl, hexyl, isohexyl and also heptyl, octyl, nonyl and decyl as well as their linear or branched position isomers, the term linear or branched alkenyl radical designates the following radicals: vinyl, allyl, 1-propenyl, butenyl, 1-butenyl, pentenyl or hexenyl as well as their linear or branched position isomers, the term saturated or unsaturated cyclic radical constituted by 3 to 7 members and optionally containing one or more identical or different heteroatoms, chosen from oxygen, sulphur or nitrogen atoms designates on the one hand a cycloalkyl radical which itself designates in particular the cyclopentyl and cyclohexyl radicals or a carbocyclic radical interrupted by one or more heteroatoms chosen from oxygen, nitrogen or sulphur atoms such as quite particularly the dioxolane, dioxane, dithiolane, thiooxolane or thiooxane radical, on the other hand the phenyl, thienyl, furyl, pyridyl or tetrazolyl radicals radical, the term linear or branched alkoxy radical designates the following radicals: methoxy, ethoxy, propoxy, isopropoxy, linear, secondary or tertiary butoxy, pentoxy or hexoxy as well as their linear or branched position isomers, the term alkylthio radical designates radicals in which the alkyl radical is as defined above such as for example in methylthio, ethylthio, propylthio, isopropylthio, butylthio, sec-butylthio, tert-butylthio, isopentylthio, isohexylthio, but also heptylthio, octylthio, nonylthio or decylthio as well as their linear or branched position isomers, the cycloalkylthio radical in particular designates cyclopentylthio and cyclohexylthio radicals.

Among the alkoxyalkyl radicals the following radicals can be mentioned: methoxymethyl, ethoxymethyl, methoxyethyl, ethoxypropyl, propyloxymethyl, propyloxypropyl or also propyloxyethyl.

The alkyl and alkoxyalkyl radicals as defined above can be substituted by a free, salified or esterified carboxy radical to give the corresponding carboxyalkyl and carboxyalkoxyalkyl radicals, the term halogen atom preferably designates the chlorine atom, but can also represent a fluorine, bromine or iodine atom, the term acid function or acid isosteric function designates the free, salified or esterified carboxy radical, the free or salified tetrazolyl radical, or the following radicals:
$SO_3H$, $—PO(OH)_2$,
$NHSO_2—CF_3$
$NH—SO_2—NH—V$
$NH—SO_2—NH—CO—V$
$NH—CO—V$
$NH—CO—NH—V$
$NH—CO—NH—SO_2—V$
$SO_2—NH—V$
$SO_2—NH—CO—V$
$SO_2—NH—CO—NH—V$
$CONH—V$
$CO—NH—OH$
$CONH—SO_2—V$
in which V represents a linear or branched alkyl or alkenyl radical containing at most 6 carbon atoms or a phenyl, pyridyl, pyrimidinyl, piperazinyl, thienyl or tetrazolyl radical, the alkyl, alkenyl and phenyl radicals being optionally substituted by one or more radicals chosen from halogen atoms and hydroxy, alkoxy or phenyl radicals, all the phenyl radicals and the piperazinyl radical being optionally substituted by a linear or branched alkyl radical containing at most 4 carbon atoms.

The carboxy radical or radicals of the products of formula (I) can be salified or esterified by various groups known to a man skilled in the art amongst which there can be mentioned, for example:

among the salification compounds, mineral bases such as, for example, an equivalent of sodium, potassium, lithium, calcium, magnesium or ammonium or organic bases such as, for example, methylamine, propylamine, trimethylamine, diethylamine, triethylamine, N,N-dimethylthanolamine, tris (hydroxymethyl) amino methane, ethanolamine, pyridine, picoline, dicyclohexylamine, morpholine, benzylamine, procaine, lysine, arginine, histidine, N-methylglucamine.

The sodium or potassium salts are preferred.

among the esterification compounds, alkyl radicals to form alkoxy carbonyl groups such as, for example, methoxycarbonyl, ethoxycarbonyl, tert-butoxycarbonyl or benzyloxycarbonyl, these alkyl radicals being able to be substituted by radicals chosen for example from halogen atoms, hydroxyl, alkoxy, acyl, acyloxy, alkylthio, amino or aryl radicals such as, for example, in the following groups: chloromethyl, hydroxypropyl, methoxymethyl, propionyloxymethyl, methylthiomethyl, dimethylaminoethyl, benzyl or phenethyl.

There can be mentioned radicals formed with the remainders of easily cleavable esters such as methoxymethyl, ethoxymethyl radicals; acyloxyalkyl radicals such as pivaloyloxymethyl, pivaloyloxyethyl, acetoxymethyl or acetoxyethyl; alkyloxycarbonyloxy alkyl radicals such as methoxycarbonyloxy methyl or ethyl, isopropyloxycarbonyl methyl or ethyl.

A list of such ester radicals can be found for example in the European Patent EP 0,034,536.

The addition salts with mineral or organic acids of the products of formula (I) can be, for example, the salts formed with the following acids: hydrochloric, hydrobromic, hydroiodic, nitric, sulphuric, phosphoric, propionic, acetic, formic, benzoic, maleic, fumaric, succinic, tartaric, citric, oxalic, glyoxylic, aspartic, ascorbic, alkylmonosulphonic such as for example methanesulphonic, ethanesulphonic, propanesulphonic, alkyldisulphonic such as for example methanedisulphonic, alpha, beta-ethanedisulphonic, arylmonosulphonic such as benzenesulphonic and aryldisulphonic.

More particularly there can be mentioned the salts formed with hydrochloric or methanesulphonic acids for example.

It should be remembered that stereoisomerism can be defined in the broadest sense of the term as the isomerism of compounds having the same developed formulae, but whose different groups are arranged differently in space, such as in particular in the boat and chair shapes of cyclohexane and monosubstituted cyclohexanes whose substituent can be in axial or equatorial position, and the different possible rotational conformations of ethane derivatives. However, another type of stereoisomerism exists, due to the different spatial arrangements of fixed substituents, either on double bonds, or on rings, which is often called geometrical isomerism or cis-trans isomerism. The term stereoisomerism is used in the present Application in its broadest sense and therefore relates to all of the compounds indicated above.

Therefore a subject of the present invention is the products of formula (I) as defined above, in which A, B and R have the meanings indicated above and $R_1$ represents a freeor esterified carboxy radical or a free or esterified tetrazolyl radical, said products of formula (I) being in all possible racemic, enantiomeric and diastereoisomeric isomer forms, as well as the addition salts with mineral and organic acids or with mineral and organic bases of said products of formula (I).

A particular subject of the present invention is the products of formula (I) as defined above, in which:

A represents either a nitrogen atom substituted by a linear or branched alkyl radical containing at most 4 carbon atoms, or a methine radical substituted by a phenyl, thienyl or pyridyl radical, B represents either a nitrogen atom substituted by an alkyl radical containing at most 4 carbon atoms itself substituted by a cyclohexyl radical, itself optionally substituted by a carboxy radical or by a carboxymethoxymethyl radical, or a methine radical substituted by an alkylthio radical containing at most 6 carbon atoms or by a cyclohexylthio radical, these radicals being optionally substituted by a carboxy radical or by a phenyl radical itself substituted by an alkoxy radical containing at most 6 carbon atoms, it being understood that when one of A and B represents a nitrogen atom, the other one of A and B represents a methine radical, these radicals being substituted as indicated above, $R_1$ represents a free or esterified carboxy radical, R represents a halogen atom, said products of formula (I) being in all possible racemic, enantiomeric and diastereoisomeric isomer forms, as well as the addition salts with mineral and organic acids or with mineral and organic bases of said products of formula (I).

A more particular subject of the present invention is the products of formula (I) as defined above, in which A represents a methine radical substituted by a phenyl, thienyl or pyridyl radical, B represents a nitrogen atom substituted by a cyclohexylmethyl radical itself optionally substituted by a carboxy or carboxymethyl radical in which the carboxy radical is free or esterified, $R_1$ represents a free, esterified or salified carboxy radical or a free or salified tetrazolyl radical, R represents a hydrogen or halogen atom, said products of formula (I) being in all possible racemic, enantiomeric and diastereoisomeric isomer forms, as well as the addition salts with mineral and organic acids or with mineral and organic bases of said products of formula (I).

An even more particular subject of the present invention is the products of formula (I) as defined above, the names of which follow:

4-((6-chloro-1,3-benzodioxol-5-yl) methyl)-1-(cyclohexylmethyl) 3-phenyl 1H-pyrazole 5-carboxylic acid, 1-butyl-5-((6-chloro-1,3-benzodioxol-5-yl) methyl)-3-((5-carboxypentyl)thio)-1H-pyrazole-4-carboxylic acid, 1-((3-carboxycyclohexyl) methyl)-4-((6-chloro 1,3-benzodioxol-5-yl) methyl) 3-phenyl-1H-pyrazole-5-carboxylic acid, 4-((6-chloro-1,3-benzodioxol-5-yl) methyl)-1-(cyclohexylmethyl) 3-(2-thienyl)-1H-pyrazole 5-carboxylic acid, 4-((6-chloro-1,3-benzodioxol-5-yl) methyl)-1-(cyclohexylmethyl) 3-(2-pyridinyl)-1H-pyrazole-5-carboxylic acid, 4-((6-chloro-1,3-benzodioxol-5-yl) methyl)-1-(cyclohexylmethyl) 3-(3-thienyl)-1H-pyrazole-5-carboxylic acid, 1-butyl 3-((4-(carboxymethyl) cyclohexyl) thio) 5-((6-chloro 1,3-benzodioxol-5-yl) methyl) 1H-pyrazole 4-carboxylic acid, 3-((4-(carboxymethyl) cyclohexyl) thio) 5-((6-chloro 1,3-benzodioxol-5-yl) methyl) 1-propyl 1H-pyrazole 4-carboxylic acid, 1-((bicyclo(2.2.2)oct-2-yl) methyl) 4-((6-chloro 1,3-benzodioxol-5-yl) methyl) 3-phenyl 1H-pyrazole 5-carboxylic acid, 1-((4-carboxycyclohexyl) methyl) 4-((6-chloro 1,3-benzodioxol-5-yl) methyl) 3-(2-thienyl) 1H-pyrazole 5-carboxylic acid, cis/trans 1-((4-(carboxymethyl) cyclohexyl) methyl) 4-((6-chloro 1,3-benzodioxol-5-yl) methyl) 3-(2-thienyl) 1H-pyrazole 5-carboxylic acid, 1-((2-(carboxymethoxy) phenyl) methyl) 4-((6-chloro 1,3-benzodioxol-5-yl) methyl) 3-(2-thienyl) 1H-pyrazole 5-carboxylic acid, 1-((3-carboxycyclohexyl) methyl) 4-((6-chloro 1,3-benzodioxol-5-yl) methyl) 3-(2-thienyl) 1H-pyrazole 5-carboxylic acid.

Also a subject of the present invention is the preparation process for the products of formula (I) as defined above, characterized in that:

either a product of formula (II):

$$ZCA'—CO—CH_2—CO—CO_2alk \quad (II)$$

in which ZCA' has the meaning indicated above for ZCA in which the optional reactive functions are optionally protected, is reacted with the product of formula (III):

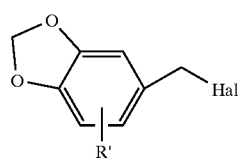

in which R' has the meaning indicated above for R in which the optional reactive functions are optionally protected, and Hal represents a halogen atom, in order to obtain the product of formula (IV):

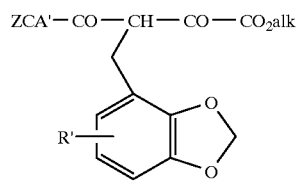

in which R', ZCA' and alk have the meanings indicated above, which is reacted with hydrazine $NH_2—NH_2$ in order to obtain a product of formula (V):

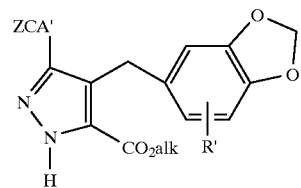

in which R', ZCA' and alk have the meanings indicated above, which is reacted with the compound of formula (VI):

$$ZNB'—W \quad (VI)$$

in which ZNB' has the meaning indicated above for ZNB in which the optional reactive functions are optionally protected and W represents a halogen atom or a tosyl radical, in order to obtain the product of formula ($I_1$):

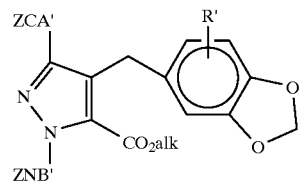

or a product of formula (VII):

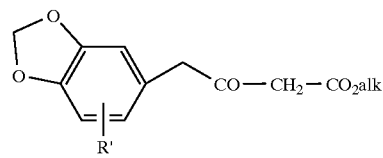

in which R' and alk have the meanings indicated above, is reacted with carbon disulphide and a product of formula (VIII):

$$R_d—Hal \quad (VIII)$$

in which $R_d$ represents an optionally substituted alkyl radical and Hal represents a halogen atom, in order to obtain the product of formula (IX):

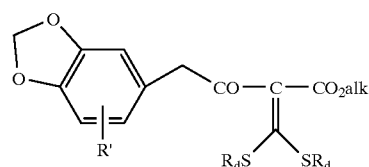

in which R', alk and $R_d$ have the meanings indicated above and S represents a sulphur atom, which is treated with a product of formula (X):

$$ZNA'—NH—NH_2 \quad (X)$$

in which ZNA' has the meaning indicated above for ZNA in which the optional reactive functions are optionally protected, in order to obtain the product of formula (I₂):

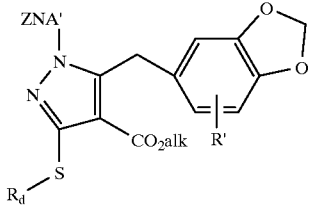

(I₂)

in which ZNA', alk, R_d and S have the meanings indicated above, or a product of formula (XI):

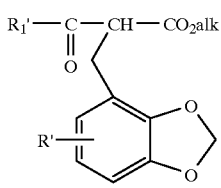

(XI)

in which R' and alk have the meanings indicated above and R'₁ has the meaning indicated above for R₁, in which the optional reactive functions are optionally protected, is reacted with the following hydrazine derivative:

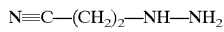

N≡C—(CH₂)₂—NH—NH₂ in order to obtain a product of formula (XII):

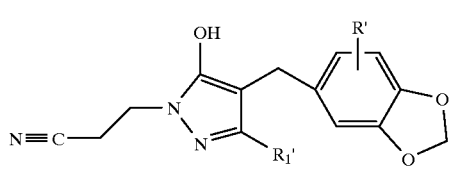

(XII)

in which R' and R'₁ have the meanings indicated above, which is converted into a product of formula (XIII):

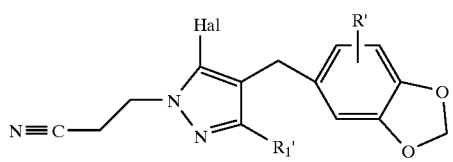

(XIII)

in which Hal, R' and R'₁ the have meanings indicated above, which is subjected to the action of a base then to the action of a compound of formula (VI) as defined above, in order to obtain the product of formula (XIV):

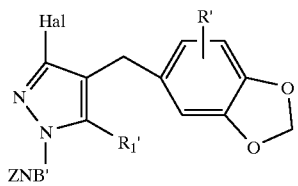

(XIV)

in which R', R'₁, ZNB' and Hal have the meanings indicated above, which is subjected to a substitution reaction by a derivative of boronic acid or by an organometallic compound, on the halogen atom in order to obtain the product of formula (I₃):

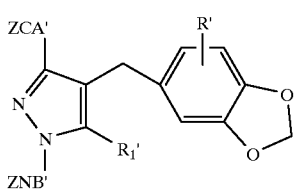

(I₃)

in which ZCA', ZNB', R' and R'₁ have the meanings indicated above, or the product of formula (VII) as defined above is reacted with a product of formula (XV):

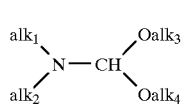

(XV)

in which alk₁, alk₂, alk₃ and alk₄, identical or different, represent an alkyl radical, in order to obtain a product of formula (XVI):

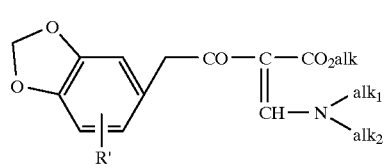

(XVI)

in which R', alk, alk₁ and alk₂ have the meanings indicated above, which is treated with hydrazine, in order to obtain the product of formula (XVII):

(XVII)

in which R' and alk have the meanings indicated above, which is treated by a halogenation agent in order to obtain a product of formula (XVIII):

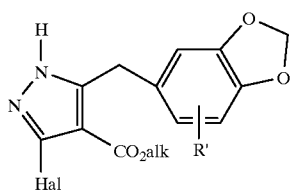

(XVIII)

in which R', Hal and alk have the meanings indicated above, which is treated with the product of formula (XIX):

 (XIX)

in which ZNA' and Hal have the meanings indicated above, in order to obtain the product of formula (XX):

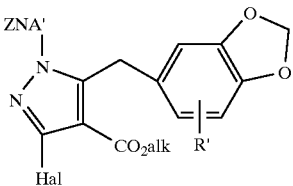

(XX)

in which R' and alk have the meanings indicated above, on which a product of formula (XXI):

ZCB'—M                                    (XXI)

in which ZCB' has the meaning indicated above, and M represents a metal or a boron atom is reacted, in order to obtain the product of formula (I₄):

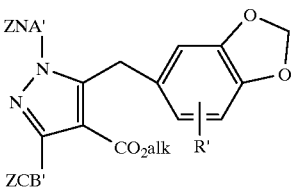

(I₄)

in which R', alk, ZNA' and ZCB' have the meanings indicated above,
which products of formulae (I₁), (I₂), (I₃) and (I₄) as defined above can be subjected, if desired and if necessary, to one or more of the following conversion reactions, in any order:

a) a saponification reaction of the ester function into an acid function,
b) a conversion reaction of the carbamoyl radical into a nitrile radical,
c) a conversion reaction of the nitrile radical into a tetrazolyl,
d) an oxidation reaction of the alkylthio group into the corresponding sulphoxide or sulphone, then if appropriate, conversion of the sulphoxide into an —SH function and if appropriate into —S—$Z_B$ in which $Z_B$ represents an alkyl or cycloalkyl radical as defined above, among the values of B in which the optional reactive functions are optionally protected,
e) a conversion reaction of a carbamate into urea and in particular of a sulphonylcarbamate into sulphonylurea,
f) a conversion reaction of the ester function into a hydroxyalkyl or alkoxyalkyl radical then into an alkyl radical derivative,
g) a reaction to eliminate the protective groups that can be carried by the protected reactive functions,
h) a salification reaction by a mineral or organic acid or by a base in order to obtain the corresponding salt,
i) a resolution reaction of the racemic forms into resolved products, said products of formula (I) thus obtained being in all possible racemic, enantiomeric and diastereoisomeric isomer forms.

It can be noted that such conversion reactions of substituents into other substituents can also be carried out on the starting products as well as on the intermediates as defined above before continuing the synthesis according to the reactions indicated in the process described above.

Under preferred conditions for implementing the invention, the process described above can be carried out in the following manner:

the action of the products of formula (III) on the products of formula (II), in order to obtain the products of formula (IV) is carried out in the presence of a strong base or a carbonate: for example the operation can be carried out in the presence of sodium hydride or ethylate in an aprotic solvent such as toluene or also in the presence of sodium or potassium carbonate for example in dimethylformamide.

The conditions relating to this reaction are described for example in J. Org. Chem. Vol. 39, No. 22, (1974), p. 3271.

In the compound of formula (III), Hal preferably represents a chlorine, bromine or iodine atom.

The operation can be carried out in the presence of a catalyst such as aliquat 336 and potassium iodide in particular when Hal represents a chlorine atom.

The action of hydrazine or its derivatives, in particular of the products of formula (X), on the products of formula (IV), (IX), (XI) or (XVI) in order to obtain the products of formula (V), (I₂), (XII) or (XVII) respectively can be carried out in the presence of an acid such as acetic acid under reflux or also in an alcohol such as methanol or ethanol.

When the hydrazine derivatives are in the form of a hydrazine salt which can be for example the hydrochloride, the operation is preferably carried out in the presence of a base such as soda or ammonium hydroxide in order to obtain, first of all, the free base.

The OH radical of the product of formula (XII) is converted into a halogen atom for example by the action of phosphorus oxychloride or oxybromide to produce the product of formula (XIII).

The reaction of the product of formula (XIII) thus obtained with the compound of formula (VI) in order to obtain the product of formula (XIV) can be carried out by the action beforehand of a base such as for example sodium hydride in a solvent such as dimethylformamide then by the action of the product of formula (VI) in which the halogen atom can be in particular a bromine atom.

The reaction of the compound of formula (XIV) thus obtained with a derivative of boronic acid or an organometallic compound in order to obtain a product of formula (I₃) can be carried out in the presence a catalyst such as palladium in a solvent, such as for example dimethylformamide or toluene.

An illustration of such reactions is given in the preparation of Examples 8, 9 and 10 described hereafter.

The reaction of the product of formula (VII) with the product of formula (VIII) and carbon disulphide in order to obtain the product of formula (IX) can be carried out in the presence of potassium fluoride on alumina.

The reaction of the product of formula (VII) with the product of formula (XV) in order to obtain the product of formula (XVI) can be carried out by simple introduction of the two products preferably hot.

Halogenation of the product of formula (XVII) into the product of formula (XVIII) can be carried under the usual conditions by a halogenation agent such as for example bromine in acetic acid.

The reaction of the product of formula (XX) with the product of formula (XXI) in order to obtain the product of formula ($I_4$) can be carried out under the usual conditions for a organo metallic compound such as for example an organozinc, organostannane or an organoboronic acid, in the presence of a catalyst such as for example palladium tetrakis.

In the compound of formula (XXI), M preferably represents zinc, tin or a boron atom: as an example of such a compound, there can be mentioned iodo benzyl zinc compound.

In the compounds of formulae (VI) and (XIX), Hal represents a halogen atom but could also be a pseudo-halogen such as a tosyl or a mesyl.

The reaction of the product of formula (V) with the product of formula (VI) in order to obtain a product of formula ($I_1$) or the reaction of the product of formula (XVIII) with the product of formula (XIX) in order to obtain the product of formula (XX) can be carried out for example hot in an aprotic solvent such as toluene or dimethylformamide, with for example an alkyl halide such as methyl iodide or cyclohexylmethyl bromide or also with ethyl 1-[(3-tosyl-methyl) cyclohexyl] carboxylate in the presence of a base such as for example sodium hydride or sodium or potassium carbonate.

The products of formulae ($I_1$), ($I_2$), ($I_3$) and ($I_4$) constitute products of formula (I) and can be converted into other products of formula (I) by being subjected to one or more of the reactions a) to i) indicated above.

Thus the various reactive functions which can be carried by some of the compounds of the reactions defined above can, if necessary, be protected: it concerns for example the hydroxyl, acyl, free carboxy radicals or also the amino and monoalkylamino radicals which can be protected by the appropriate protective groups.

The following non-exhaustive list of examples of the protection of the reactive functions can be mentioned:
the hydroxyl groups can be protected for example by alkyl radicals such as tert-butyl, trimethylsilyl, tertbutyldimethylsilyl, methoxymethyl, tetrahydropyrannyl, benzyl or acetyl,
the amino groups can be protected for example by acetyl, trityl, benzyl, tert-butoxycarbonyl, phthalimido radicals or other radicals known in the chemistry of the peptides,
the acyl groups such as the formyl group can be protected for example in the form of cyclic or non-cyclic ketals or thioketals such as dimethyl or diethylketal or ethylene dioxyketal, or diethylthioketal or ethylenedithioketal,
the acid functions of the products described above can, if desired, amidified by a primary or secondary amine for example in methylene chloride in the presence, for example, of 1-ethyl-3-(dimethylaminopropyl) carbodiimide hydrochloride at ambient temperature:
the acid functions can be protected for example in the form of esters formed with easily cleavable esters such as benzyl or terbutyl esters or esters known in the chemistry of the peptides.

The reactions to which the products of formulae ($I_1$), ($I_2$), ($I_3$) and ($I_4$), as defined above, can be subjected, if desired or if necessary, can be carried out, for example, as indicated hereafter:

a) The optional conversions of the ester functions into an acid function of the products described above can be, if desired, carried out under the usual conditions known to a man skilled in the art in particular by acid or alkaline hydrolysis for example by soda or potash in an alcoholic medium such as, for example, in methanol or also by sulphuric or hydrochloric acid, b) the conversion reactions of the carbamoyl radical into a nitrile radical are carried out according to the usual conditions known to a man skilled in the art, such as for example passage via the keto nitrile and displacement by an amine (Chem. Comm. 1971, p. 733).

c) The optional nitrile functions of the products described above can be, if desired, converted into tetrazolyl under the usual conditions known to a man skilled in the art such as for example by the cycloaddition of a metal azide such as for example sodium azide or a trialkyltin azide on the nitrile function as indicated in the method described in the article referenced as follows:

J. Organometallic Chemistry., 33, 337 (1971) KOZIMA S. et al.

d) The optional alkylthio groups of the products described above can be, if desired, converted into the corresponding sulphoxide or sulphone functions under the usual conditions known to a man skilled in the art such as for example by peracids such as for example peracetic acid or metachloroperbenzoic acid or also by ozone, oxone, sodium periodate in a solvent such as for example methylene chloride or dioxane at ambient temperature.

The obtaining of the sulphoxide function can be encouraged by an equimolar mixture of the product containing an alkylthio group and a reagent such as in particular a peracid.

The obtaining of the sulphone function can be encouraged by a mixture of the product containing an alkylthio group with an excess of the reagent such as in particular a peracid.

The conversion of the sulphoxide into a thiol is obtained using the PUMMERER reaction for example in the presence of trifluoroacetic anhydride; the conversion of the SH substituent into $SZ_2$ can be obtained by the action of a halogenated derivative Hal-$Z_2$ for example ethyl 6-bromohexanoate.

e) The conversion reaction of a carbamate into urea and in particular of a sulphonylcarbamate into sulphonylurea, can be carried out for example under reflux of a solvent such as for example toluene in the presence of the appropriate amine.

f) The conversion reaction of the ester function as defined above can be carried out under the usual conditions known to a man skilled in the art.

g) The elimination of the protective groups such as for example those indicated above can be carried out under the usual conditions known to a man skilled in the art in particular by an acid hydrolysis carried out with an acid such as hydrochloric, benzene sulphonic or para-toluene sulphonic, formic or trifluoroacetic acid or also by catalytic hydrogenation.

The phthalimido group can be eliminated by hydrazine.

A list of the different protective group which can be used will be found for example in the BF U.S. Pat. No. 2,499,995.

h) The products described above can, if desired, be subjected to salification reactions for example by a mineral or organic acid or by a mineral or organic base according to the usual methods known to a man skilled in the art.

i) The optional optically-active forms of the products described above can be prepared by resolution of the racemics according to the usual methods known to a man skilled in the art.

Illustrations of such reactions defined above are given in the preparation of examples described hereafter.

It can be noted that the reactions indicated above in particular in b), c) and e) allow the products of formula (I) as defined above to be obtained in which $R_1$ represents the different values indicated above.

The compounds of formula (I) as defined above as well as their addition salts with acids have useful pharmacological properties.

The products of formula (I) as defined above, are endowed with antagonistic properties for the endothelin receptors and are thus in particular inhibitors of the effects of endothelin, in particular the vaso-constrictive and hypertensive effects induced by endothelin. In particular an anti-ischemic effect can be noted, the vasoconstrictive activity of the endothelin being eliminated.

The products of formula (I) are also capable of opposing the stimulating effects of endothelin at the level of all cell types, in particular smooth muscle cells, fibroblasts, neuronal cells and bone cells.

These properties justify their use in therapeutics and also a subject of the invention is as medicaments, the products as defined by formula (I) above, said products of formula (I) being in all possible racemic, enantiomeric and diastereoisomeric isomer forms, as well as the addition salts with pharmaceutically acceptable mineral and organic acids or mineral and organic bases of said products of formula (I).

A particular subject of the invention is as medicaments, the products of formula (I) as defined above, in which:

A represents either a nitrogen atom substituted by a linear or branched alkyl radical containing at most 4 carbon atoms, or a methine radical substituted by a phenyl, thienyl or pyridyl radical, B represents either a nitrogen atom substituted by an alkyl radical containing at most 4 carbon atoms itself substituted by a cyclohexyl radical, itself optionally substituted by a carboxy radical or by a carboxymethoxymethyl radical, or a methine radical substituted by an alkylthio radical containing at most 6 carbon atoms or by a cyclohexylthio radical, these radicals being optionally substituted by a carboxy radical or by a phenyl radical itself substituted by an alkoxy radical containing at most 6 carbon atoms, it being understood that when one of A and B represents a nitrogen atom, the other one of A and B represents a methine radical, these radicals being substituted as indicated above, $R_1$ represents a free or esterified carboxy radical, R represents a halogen atom, said products of formula (I) being in all possible racemic or optically-active isomer forms, as well as the addition salts with pharmaceutically acceptable mineral and organic acids or mineral and organic bases of said products of formula (I).

In particular a subject of the invention is as medicaments, the products of formula (I) as defined above, in which A represents a methine radical substituted by a phenyl, thienyl or pyridyl radical, B represents a nitrogen atom substituted by a cyclohexylmethyl radical itself optionally substituted by a carboxy or carboxymethyl radical in which the carboxy radical is free or esterified, $R_1$ represents a free, esterified or salified carboxy radicalor a free or salified tetrazolyl radical, R represents a hydrogen or halogen atom, said products of formula (I) being in all possible racemic or optically-active isomer forms, as well as the addition salts with pharmaceutically acceptable mineral or organic acids or mineral and organic bases of said products of formula (I).

A more particular subject of the invention is, as medicaments, the products described hereafter in the examples and in particular the products of formula (I) the names of which follow:

4-((6-chloro-1,3-benzodioxol-5-yl) methyl)-1-(cyclohexylmethyl) 3-phenyl 1H-pyrazole 5-carboxylic acid, 1-butyl-5-((6-chloro-1,3-benzodioxol-5-yl) methyl)-3-((5-carboxypentyl)thio)-1H-pyrazole-4-carboxylic acid, 1-((3-carboxycyclohexyl) methyl)-4-((6-chloro 1,3-benzodioxol-5-yl) methyl) 3-phenyl-1H-pyrazole-5-carboxylic acid, 4-((6-chloro-1,3-benzodioxol-5-yl) methyl)-1-(cyclohexylmethyl) 3-(2-thienyl)-1H-pyrazole 5-carboxylic acid, 4-((6-chloro-1,3-benzodioxol-5-yl) methyl)-1-(cyclohexylmethyl) 3-(2-pyridinyl)-1H-pyrazole-5-carboxylic acid, 4-((6-chloro-1,3-benzodioxol-5-yl) methyl)-1-(cyclohexylmethyl) 3-(3-thienyl)-1H-pyrazole-5-carboxylic acid, 1-butyl 3-((4-(carboxymethyl) cyclohexyl thio) 5-((6-chloro-1,3-benzodioxol-5-yl) methyl) 1H-pyrazole 4-carboxylic acid, 3-((4-(carboxymethyl) cyclohexyl) thio) 5-((6-chloro 1,3-benzodioxol-5-yl) methyl) 1-propyl 1H-pyrazole 4-carboxylic acid, 1-((bicyclo(2.2.2)oct-2-yl) methyl) 4-((6-chloro 1,3-benzodioxol-5-yl) methyl) 3-phenyl 1H-pyrazole 5-carboxylic acid, 1-((4-carboxycyclohexyl) methyl) 4-((6-chloro 1,3-benzodioxol-5-yl) methyl) 3-(2-thienyl) 1H-pyrazole 5-carboxylic acid, cis/trans 1-((4-(carboxymethyl) cyclohexyl) methyl) 4-((6-chloro 1,3-benzodioxol-5-yl) methyl) 3-(2-thienyl) 1H-pyrazole 5-carboxylic acid, 1-((2-(carboxymethoxy) phenyl) methyl) 4-((6-chloro 1,3-benzodioxol-5-yl) methyl) 3-(2-thienyl) 1H-pyrazole 5-carboxylic acid, 1-((3-carboxycyclohexyl) methyl) 4-((6-chloro 1,3-benzodioxol-5-yl) methyl) 3-(2-thienyl) 1H-pyrazole 5-carboxylic acid, as well as their addition salts with pharmaceutically acceptable mineral or organic acids or with mineral and organic bases.

The medicaments, which are a subject of the invention, for example, can be used in the treatment of all vascular spasms, in the treatment of the effects of a cerebral haemorrhage, in the treatment of coronary spasms, peripheral vascular spasms as well as in the treatment of renal insufficiencies. These medicaments can also be used in the treatment of myocardial infarction, congestive cardiac insufficiency, in the prevention of the recurrence of post-angioplastic stenosis, the prevention of cardiac and vascular fibroses, in the treatment of the atherosclerosis and certain forms of hypertension such as in particular pulmonary hypertension, as well as in the treatment of asthma.

The medicaments, which are a subject of the invention, can also be used in the treatment of the osteoporosis, prostatic hyperplasia and as neuronal protectors.

The invention extends to the pharmaceutical composition containing at least of the medicaments as defined above as active ingredient.

These pharmaceutical compositions can be administered by buccal, rectal route, by parenteral route or by local route as a topical application on the skin and mucous membranes or by injection by intravenous or intra-muscular route.

These compositions can be solid or liquid and be presented in all the pharmaceutical forms commonly used in human medicine, such as for example, plain or sugar-coated tablets, capsules, granules, suppositories, injectable preparations, ointments, creams, gels and aerosol preparations; they are prepared according to the usual methods. The active ingredient can be incorporated with excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

The usual dose, variable according to the product used, the patient being treated and the illness in question, can be, for example, 1 to 300 mg per day for an adult, by oral route or 1 to 100 mg per day by intravenous route.

The starting products of formulae (II), (III), (VI), (VII), (VIII), (X), (XI), (XV), (XIX) and (XXI) are in the main commercially available or can be prepared from commercially-available products by the usual methods known to a man skilled in the art.

As examples and in a non-exhaustive manner, the following can be mentioned:

- among the products of formula (II), ethyl benzoyl pyruvate or corresponding products in which the phenyl radical is replaced by a thienyl or pyridyl radical,
- among the products of formula (VII), there can be mentioned the derivative of ethyl acetoacetate in which R' represents a hydrogen or halogen atom,
- among the products of formula (XI), there can be mentioned the compound in which $R'_1$ represents an esterified carboxy radical or a tetrazolyl radical,
- among the products of formula (XIX), there can be mentioned cyclohexylmethyl or carboxycyclohexylmethyl bromide,
- among the products of formula (XV), there can be mentioned dimethylformamide dimethylacetal,
- among the products of formula (III), there can be mentioned in particular 6-chloro piperonyl chloride which is a commercial product, piperonyl chloride, 3,4-dichlorobenzyl chloride, or also 3-chlorobenzyl bromide,
- among the products of formula (III) which are not commercially available, 5-chloropiperanyl chloride can be prepared according to the usual methods known to a man skilled in the art,
- among the products of formulae (VIII) and (XIX), there can be mentioned methyl, butyl or cycloalkyl iodide or also for the product of formula (XIX) vinyl chloride,
- among the products of formulae (X), there can be mentioned methyl-, butyl- or butenyl-hydrazine in particular in the form of the hydrochloride prepared from hydrazine in the usual way,
- among the products of formula (XXI), there can be mentioned butyl- or cyclohexyl-magnesium.

The examples described hereafter in the experimental part give illustrations, which moreover are non-exhaustive, of such starting products.

Finally a subject of the present invention is as new industrial products, the compounds of formulae (XII), (XIII) and (XIV), when $R'_1$ is different from carboxy, as well as the products of formula (XX).

Thus a particular subject of the invention is the use of the products of formula (I) as defined above, for the preparation of pharmaceutical compositions intended for the treatment of illnesses resulting from an abnormal stimulation of the endothelin receptors.

A more particular subject of the invention is the use of the products of formula (I) as defined above, for the preparation of pharmaceutical compositions intended for the treatment of hypertension induced by endothelin.

A quite particular subject of the invention is the use of the products of formula (I) as defined above, for the preparation of pharmaceutical compositions intended for the treatment of all vascular spasms and for the treatment of the effects of a cerebral haemorrhage and renal insufficiencies.

Also a subject of the invention is the use of the products of formula (I) as defined above, for the preparation of pharmaceutical compositions intended for the treatment of myocardial infarction, the prevention of the recurrence of post-angioplastic stenosis and the prevention of cardiac and vascular fibroses.

The following examples illustrate the invention without however limiting it.

EXAMPLE 1

4-((6-chloro-1,3-benzodioxol-5-yl) methyl)-1-(cyclohexylmethyl)-3-phenyl-1H-pyrazole-5-carboxylic acid STAGE 1: ethyl beta-benzoyl 6-chloro alpha-oxo-1,3-benzodioxol 5-butanoate 12.7 g of ethyl benzoyl pyruvate (prepared as indicated in the publication Tetrahedron Letter, 29, (1988), 3997–4000), 100 ml of dimethylformamide, 3 g of sodium ethylate are introduced, agitation is carried out at ambient temperature for 15 minutes then 11.81 g of 6-chloropiperonyl chloride and 8.30 g of potassium iodide are added. Agitation is carried out at ambient temperature for 24 hours, the whole is poured into 100 ml of water, followed by extraction with 3×50 ml of ethyl acetate, washing with 50 ml of sodium chloride and drying. In this way 22.8 g of expected product is obtained and used as it is for the following stage.

STAGE 2: ethyl 4-((6-chloro 1,3-benzodioxol-5-yl) methyl)-5-phenyl 1H-pyrazole-3-carboxylate 2.8 ml of hydrazine hydrate is added to 22.8 g of the product obtained in Stage 1 above, in 114 ml of ethanol and the reaction medium is heated for 4 hours under reflux. After cooling down to ambient temperature, separating and rinsing with ethanol, 9.11 g of expected product is obtained. M.p.=204° C.

STAGE 3: ethyl 4-((6-chloro-1,3-benzodioxol-5-yl) methyl)-1-(cyclohexylmethyl)-3-phenyl-1H-pyrazole-5-carboxylate 25 mg of sodium hydride is added to 192 mg of the product obtained in Stage 2 above, in 2 ml of dimethylformamide then agitation is carried out for 15 minutes at ambient temperature. 0.087 ml of 1-bromo (1-cyclohexyl) methyl is added, agitation is carried out for 20 hours, the reaction medium is poured into water, extracted with ethyl acetate, the extracts are washed with an aqueous solution of sodium chloride, dried and the solvent is evaporated off under reduced pressure. The residue is chromatographed on silica (eluant: methylene chloride - ethyl acetate: 95-5) and the expected product is obtained i.e. 138 mg of isomer A, M.p.=130° C. and 39 mg of isomer B (amorphous).

STAGE 4: 4-((6-chloro-1,3-benzodioxol-5-yl) methyl)-1-(cyclohexylmethyl)-3-phenyl-1H-pyrazole-5-carboxylic acid 120 mg of isomer A obtained in Stage 3 above in 5 ml of ethanol is agitated for 16 hours at ambient temperature in the presence of 0.46 ml of 2 N soda. The solvents are evaporated off, the residue is taken up in 5 ml of water, followed by filtering, neutralizing by the addition of 2 N hydrochloric acid, the precipitate is filtered off, rinsed with water and 90 mg of expected product is collected. M.p.=234° C. IR Spectrum (CHCl$_3$ cm$^{-1}$) C=O 1686 Heterocycle+aromatic 1600-1520-1504

EXAMPLE 2

1-butyl-5-((6-chloro-1,3-benzodioxol-5-yl) methyl)-3-((5-carboxypentyl) thio)-1H-pyrazole-4-carboxylic acid STAGE 1: 6-chloro-1,3-benzodioxole-5-acetonitrile 1.025 g of 6-chloropiperonyl chloride, 5 ml of dimethylformamide, 330 mg of potassium cyanide are introduced, agitation is carried out at ambient temperature for 6 hours, the reaction medium is poured into 50 ml of water, extracted with 3×30 ml of ethyl acetate, the extracts are washed with 30 ml of sodium chloride and dried. After recrystallization from 5 ml of isopropyl ether under reflux and separating, 740 mg of expected product (white crystals) is obtained. ANALYSIS: IR CHCl$_3$ cm$^{-1}$ CN 2255 Aromatic 1625-1505-1481

STAGE 2: ethyl 6-chloro-beta-oxo-1,3-benzodioxole-5-butanoate 8.3 g of electrolytic zinc and 10 ml of tetrahydrofuran are introduced. The zinc is activated by the addition of 0.2 ml of 1,2-dibromoethane and 5 minutes under reflux. After cooling down, 5 g of the product obtained as indicated in Stage 1 above and 40 ml of tetrahydrofuran are added, the reaction medium is taken to reflux and 11.4 ml of ethyl bromoacetate is added over 1 hour, agitation is carried out again for 15 minutes under reflux, followed by cooling down to 0+5° C. and hydrolysis using 25 ml of hydrochloric acid. After agitation for 30 minutes, the reaction medium is poured into 250 ml of water, extracted with 100+2×50 ml of ethyl acetate, the extracts are washed with 50 ml of sodium chloride and dried. Recrystallization is carried out from 96% ethanol, followed by chromatography on silica eluting with methylene chloride - ethyl acetate: 95-5. In this way 885 mg of expected product is obtained. ANALYSIS: IR CHCl$_3$ cm$^{-1}$ C+O 1741-1720 Aromatic 1625-1507-1482

STAGE 3: ethyl alpha-[bis(methylthio)methylene]-6-chlorobeta-oxo-1,3-benzodioxole-5-butanoate a) Preparation of Potassium Fluoride on Alumina 20 g of of potassium fluoride is dissolved in 200 ml of water, then 30 g of neutral activated alumina is added. After agitation for a few minutes, the reaction medium is dried by taking up several times in 100% ethanol then dried. In this way 50 g of potassium fluoride on alumina is obtained.

b) Obtaining the Cetene Thioacetal 570 mg of the product obtained in Stage 2 above, 20 ml of acetonitrile, 1.6 g of the product prepared above in a), and 0.12 ml of carbon disulphide are introduced, agitation is carried out at ambient temperature for 1 hour then 0.25 ml of methyl iodide is introduced and agitation is carried out at ambient temperature for 16 hours. The reaction medium is filtered, rinsed 3 times with acetonitrile and dried, followed by taking up in 20 ml of methylene chloride, filtering and drying. After chromatography on silica in methylene chloride, 600 mg of expected product (yellow solid) is obtained. M.p.=70° C. ANALYSIS: IR CHCl$_3$-Nujol cm$^{-1}$ C=O 1704 C=C+Aromatic 1627-1526-1505-1482

STAGE 4: ethyl 1-butyl-3-((6-chloro-1,3-benzodioxol-5-yl) methyl)-5-(methylthio)-1H-pyrazole-4-carboxylate (A) ethyl 1-butyl-2-((6-chloro-1,3-benzodioxol-5-yl)methyl)-4-(methylthio)-1H-pyrazole-3-carboxylate (B)

150 mg of the product obtained in Stage 3 above, 5 ml of ethanol and 136 mg of butylhydrazine oxalate are introduced, the reaction medium is taken to reflux and agitation is carried out for 3 days followed by drying. Chromatography on silica is carried out eluting with cyclohexane-acetate of ethyl: 9-1. In this way 21 mg of the expected product A (resin) and 45 mg of the expected product B are obtained. ANALYSIS: Product A IR CHCl$_3$ cm$^{-1}$ C=O 1702 Aromatic+Heterocycle 1625-1505-1483

STAGE 5: ethyl 1-butyl 5-((6-chloro 1,3-benzodioxol-5-yl) methyl) 3-(methylsulphinyl)-1H-pyrazole-4-carboxylate 250 mg of the ethyl ester obtained from the product obtained as indicated in Stage 4 above is dissolved in 5 ml of dichloromethane, the reaction medium is cooled down to 0° C. and 180 mg of metachloroperbenzoic acid in solution in 8 ml of dichloromethane is added and agitation is carried out for 45 minutes. The reaction medium is washed with a solution of sodium bicarbonate, followed by extraction with dichloromethane, the organic phase is washed with water, dried and the solvent is evaporated off under reduced pressure. The crude product is obtained which is chromatographed on silica (eluant: dichloromethane-methanol 97.5-2.5). 178 mg of expected product is obtained. M.p.=82° C.

STAGE 6: ethyl 1-butyl-5-((6-chloro-1,3-benzodioxol-5-yl) methyl) 3-mercapto-1H-pyrazole-4-carboxylate 169.3 mg of product obtained in Stage 5 above is dissolved in 20 ml of dichloromethane and 0.11 ml of trifluoroacetic anhydride is added. Agitation is carried out for 15 minutes, the solvent is evaporated off under reduced pressure, the residue is taken up in 2 ml of methanol and 0.55 ml of triethylamine and agitation is carried out again for 15 minutes at ambient temperature, followed by extraction with dichloromethane, the organic phase is washed with a saturated aqueous solution of ammonium chloride, dried and the solvent is evaporated off under reduced pressure and 125 mg of expected product is collected.

STAGE 7: ethyl 1-butyl 5-((6-chloro 1,3-benzodioxol-5-yl) methyl) 3-((6-ethoxycarbonylpentyl)-thio)-1H-pyrazole-4-carboxylate 14.4 mg of sodium hydride is added to a solution containing 125 mg of the product obtained as in Stage 6 above in 2 ml of dimethylformamide. Agitation is carried out for 15 minutes then 0.056 ml of ethyl-6-bromo hexanoate is added and agitation is carried out for 5 hours at ambient temperature. 4 ml of water is added followed by extraction with ethyl acetate, washing with a saturated aqueous solution of sodium chloride, drying and the solvent is evaporated off under reduced pressure. After chromatographing on silica (eluant: methylene chloride - ethyl acetate: 95-5), 82.6 mg of expected product is obtained.

STAGE 8: 1-butyl 5-((6-chloro-1,3-benzodioxol-5-yl) methyl)-3-((5-carboxypentyl) thio)-1H-pyrazole-4-carboxylic acid 72.4 mg of the product obtained in Stage 7 above is mixed with 0.26 ml of 2 N soda and 2 ml of ethanol. Agitation is carried out for 3 hours under reflux, the organic solvents are evaporated off under reduced pressure, 4 ml of water is added, the solution is acidified using 0.26 ml of 2 N hydrochloric acid, the precipitate formed is separated out, washed with water, dried at 40° C. under reduced pressure and 49.2 mg of expected product is collected. M.p.=140° C.

EXAMPLE 3

1-butyl-5-((6-chloro-1,3-benzodioxol-5-yl) methyl)-3-(((4-methoxyphenyl) methyl) thio)-1H-pyrazole-4-carboxylic acid The operation is carried out as in Example 2 using in Stage 7 of Example 2 1-chloro-((4-methoxyphenyl) methyl)

EXAMPLE 4

4-((6-chloro-1,3-benzodioxol-5-yl) methyl) 1-(2-cyclohexylethyl)-3-phenyl)-1H-pyrazole 5-carboxylic acid The operation is carried out as in Example 1 using in Stage 3 of Example 1 1-bromo-(2-cyclohexyl) ethyl) instead of 1-bromo (1-cyclohexyl) methyl then proceeding as in Stage 4 of Example 1 and in this way the expected product is obtained. M.p. ~80° C.

EXAMPLE 5

1-((3-carboxycyclohexyl) methyl)-4-((6-chloro-1,3-benzodioxol-5-yl) methyl)-3-phenyl-1H-pyrazole-5-carboxylic acid The operation is carried out as in Example 1 using in Stage 3 of Example 1 ethyl 1-[(3-tosylmethyl) cyclohexyl] carboxylate prepared as indicated above instead of 1-bromo (1-cyclohexyl) methyl then by proceeding as in Stage 4 of Example 1 and in this way the expected product is obtained. M.p. ~130° C.

Preparation of the Tosylate used in Example 5

Formation of the Acid Chloride 5 g of 1,3-cyclohexane dicarboxylic acid in 10 ml of thionyl chloride is agitated for 3 hours under reflux, the excess reagent is distilled off, the residue is taken up in toluene, the solvent is evaporated off and 6.04 g of expected product is collected.

Formation of the Ester 1.69 ml of ethanol and 50 ml of tetrahydrofuran are cooled down to 0° C., 18.12 ml of n-butyllithium in solution in tetrahydrofuran (1.6 M/l) is added over 30 minutes and agitation is carried out for 30 minutes at 0°/+5° C. This solution is added over 30 minutes to 6.04 g of the acid chloride obtained previously in 60 ml of tetrahydrofuran at a temperature lower than 10° C.

Reduction to the Alcohol

While maintaining this temperature, 58 ml of lithium tri(terbutoxyalumino hydride) is added over 30 minutes, agitation is carried out for 1 hour, the reaction medium is poured into N hydrochloric acid, followed by extraction with ethyl acetate, washing with salt water, drying, evaporating under reduced pressure, the residue is chromatographed (eluant: $CH_2Cl_2$/AcOEt 9-1) and 1.37 g of the alcohol is obtained.

Formation of the Tosylate 1.33 g of the preceding alcohol in 5 ml of pyridine is cooled down to 0°/+5° C., 1.63 g of tosyl chloride in 5 ml of dichloromethane is added over 20 minutes and agitation is carried out for 20 hours at ambient temperature. The reaction medium is poured into 100 ml of N hydrochloric acid, followed by extraction with ethyl acetate, the extracts are washed with water, dried, the solvent is evaporated off under reduced pressure, the residue is chromatographed on silica (eluant: $CH_2Cl_2$) and 1.97 g of the expected tosylate is obtained.

EXAMPLE 6 cis-1-[[2-[(carboxymethoxy) cyclohexyl]methyl]-4-((6-chloro-1,3-benzodioxol-5-yl) methyl]-3-phenyl-1H-pyrazole-5-carboxylic acid The operation is carried out as in Example 1 using in Stage 3 of Example 1 (1-tosyl)-1-[2-((ethoxycarbonylmethoxy) methyl) cyclohexyl] methyl instead of 1-bromo (1-cyclohexyl) methyl then by proceeding as in Stage 4 of Example 1 and in this way the expected product is obtained. M.p. ~90° C.

Preparation of the Tosylate used in Example 6

Formation of the Ester 2.23 ml of ethyl diazoacetate in solution in 16 ml of dichloromethane is added over one hour at ambient temperature to 3.06 g of cis 1,2-cyclohexane dimethanol in 100 ml of dichloromethane in the presence of a few drops of ethyl etherate borotrifluoride. The reaction medium is maintained under agitation for 16 hours at ambient temperature, followed by washing with water and drying, the solvent is evaporated off under reduced pressure, the residue is chromatographed on silica (eluant: AcOEt/cyclohexane 20–80) and 1.98 g of expected product is obtained.

Formation of the Tosylate 1.01 g of the preceding product in 5 ml of pyridine is cooled down to 0°/+5° C., 1.00 g of tosyl chloride in 5 ml of dichloromethane is added over 30 minutes and agitation is carried out for 16 hours at ambient temperature. The reaction medium is poured into 100 ml of N hydrochloric acid, followed by extraction with dichloromethane, washing with water and drying, the solvent is evaporated off under reduced pressure, the residue is chromatographed on silica (eluant: cyclohexane/AcOEt 2-8) and 1.38 g of the expected tosylate is obtained.

EXAMPLE 7

1-[[1-[(carboxymethoxy) methyl]cyclohexyl] methyl]-4-((6-chloro-1,3-benzodioxol-5-yl) methyl]-3-phenyl-1H-pyrazole-5-carboxylic acid The operation is carried out as in Example 1 using in Stage 3 of Example 1 (1-bromo)-1-[1-((ethoxycarbonylmethoxy) methyl) cyclohexyl]methyl instead of 1-bromo (1-cyclohexyl) methyl then by proceeding as in Stage 4 of Example 1 and in this way the expected product is obtained. M.p. ~188° C.

Preparation of the Tosylate used in Example 7

The operation is carried out as in the preparation of the tosylate used in Example 6 using at the start 1.09 ml of ethyl diazoacetate and 1.5 g of 1,1-(cyclohexane) dimethanol and 840 mg of the intermediate ester is obtained. 820 mg of this ester is reacted with 814 mg of tosyl chloride as indicated above in Example 6 in order to obtain 1.23 g of the expected tosylate.

EXAMPLE 8

4-((6-chloro-1,3-benzodioxol-5-yl) methyl) 1-cyclohexylmethyl)-3-(2-thienyl)-1H-pyrazole-5-carboxylic acid STAGE 1: (E) ethyl 3-((6-chloro-1,3-benzodioxol-5-yl)-2-propenoate 60 ml of triethylphosphonoacetate is added dropwise to 11.6 g of sodium hydride in 100 ml of ethylene glycol dimethyl ether. Agitation is carried out for 50 minutes then, while maintaining the reaction medium at ambient temperature, 17.37 ml of 6-chloro piperonal in 370 ml of ethylene glycol dimethyl ether is added, agitation is carried out for 2 hours and 30 minutes, the precipitate is filtered out and the filtrate is evaporated to dryness and the residue is crystallized from ethanol. 46.33 g of expected product is obtained. M.p.=121° C.

STAGE 2: ethyl 6-chloro-1,3-benzodioxol-5-propanoate 43.93 g of the ester obtained in Stage 1 above in 900 ml of tetrahydrofuran and 300 ml of ethanol is cooled down to 0° C., then 25.61 g of cuprous chloride is added then over 30 minutes 6.52 g of sodium borohydride is added. Agitation is carried out for 2 hours at 0° C. then the reaction medium is poured into 1 liter of an ice-cooled aqueous solution of 3% hydrochloric acid. Agitation is carried out for 16 hours at ambient temperature, followed by filtering, washing with water, extracting with methylene chloride and drying, the solvent is evaporated off under reduced pressure, the residue is chromatographed on silica (eluant: cyclohexane-ethyl acetate, 8-2) and 25.21 g of expected product is obtained.

STAGE 3: diethyl 2-((6-chloro-1,3-benzodioxol-5-yl) methyl)-3-oxo 1,4-butanedioate 22.88 g of the product obtained in Stage 2 above, in 230 ml of toluene is heated for 30 minutes at 80° C. in the presence 18.96 g of sodium ethylate. 18 ml of diethyloxalate is added, agitation is carried out for 1 hour at 80° C., the reaction medium is cooled down to 0° C. then the whole is poured into 500 ml of an ice-cooled saturated aqueous solution of ammonium chloride with 500 ml of ethyl acetate added to it. The reaction medium is left to return to ambient temperature, the aqueous phase is extracted with ethyl acetate, the organic phases are washed with salt water and dried, the solvent is evaporated off under reduced pressure, the residue is chromatographed on silica (eluant: cyclohexane-ethyl acetate: 8-2) and 24.05 g of expected product is collected.

STAGE 4: ethyl 4-((6-chloro 1,3-benzodioxol-5-yl) methyl) 1-(2-cyanoethyl) 5-hydroxy 1H-pyrazole 3-carboxylate 10.06 g of the product obtained in Stage 3 above in 100 ml of glacial acetic acid is heated under reflux for 7 hours in the presence of 2-cyano-ethylhydrazine. The reaction medium is left to return to ambient temperature and agitation is carried out for 16 hours. The precipitate is filtered out, washed with ethanol and dried. The filtrate is evaporated to dryness, the residue is chromatographed on silica (eluant: methylene chloride-methanol: 9-1) and the residue and the dried precipitate are taken up in 90 ml of ethanol under reflux. After filtering and drying under reduced pressure, 5.49 g of expected product is collected. M.p.=192° C.

STAGE 5: ethyl 4-((6-chloro 1,3-benzodioxol-5-yl) methyl) 1-(2-cyanoethyl) 5-bromo 1H-pyrazole 3-carboxylate 26.3 g of tribromophosphate is introduced and heated to 60° C., 5.32 g of the product obtained in Stage 4 above is added and agitation is carried out for 20 minutes at 60° C. Dilution is carried out by the addition of 50 ml of ethyl acetate, the whole is poured into 500 ml of an $NH_4OH$+ice solution, followed by extraction with 3×200 ml of ethyl acetate, washing with a saturated solution of sodium chloride and drying. After chromatography on silica in cyclohexane-ethyl acetate: 5-5, 4.84 g of expected product (white solid) is obtained. M.p.=116° C. ANALYSES IR Spectrum: in $CHCl_3$ ($cm^{-1}$) Absence of OH CN 2258 C=O 1723 Aromatic+heterocycle 1622-1600-1535-1505-1482

STAGE 6: ethyl 4-((6-chloro-1,3-benzodioxol-5-yl) methyl)-1-cyclohexylmethyl)-3-(2-bromo)-1H-pyrazole 5-carboxylate 450 mg of sodium hydride at 50% in oil and 3 ml of dimethylformamide are introduced, the reaction medium is taken to 0° C. then 4.125 g of the product obtained in Stage 5 above and 8 ml of dimethylformamide are introduced over 10 minutes. Agitation is carried out at 0° C. for ¾ of an hour, then anothe 9 ml of dimethylformamide is added, agitation is carried out again for ¾ of an hour, then 3.35 ml of bromomethylcyclohexane is added progressively, the reaction medium is left to return to ambient temperature, followed by heating for 6 hours 30 minutes at (55±5)° C. and agitation is carried out again for 18 hours at ambient temperature. The whole is poured into 200 ml of saturated solution of ammonium chloride, extracted with 3×200 ml of ethyl acetate, followed by washing with a saturated solution of sodium chloride and drying. After chromatography on silica eluting with methylene chloride then cyclohexane-ethyl acetate: 9-1, 2.50 g of expected product (white crystals) is obtained. M.p.=116° C. ANALYSES IR Spectrum: in $CHCl_3$ ($cm^{-1}$) Absence of CN C=O 1718 Aromatic+heterocycle 1625-1600-1527-1505-1480.

STAGE 7: ethyl 4-((6-chloro-1,3-benzodioxol-5-yl) methyl)-1-cyclohexylmethyl)-3-(2-thienyl)-1H-pyrazole 5-carboxylate 5 ml of dimethylformamide (anhydrous), 96 mg of 2-thiophen-boronic acid, 17 mg of $Pd(Po_3)_4$ and 212.3 mg of $K_3PO_4$ then 241.9 mg of the product obtained in Stage 6 above are introduced and the reaction medium is taken to 100° C. for 24 hours.

Ethyl acetate is added, the organic phase is washed with $H_2$) saturated with ammonium chloride, with water then with water saturated with sodium chloride, dried, filtered and evaporated to dryness. After chromatography on silica eluting with methylene chloride-cyclohexane: 1-1, 124.5 mg of expected product (oily-solid) is obtained. ANALYSES IR Spectrum: in $CHCl_3$ ($cm^{-1}$) >=O 1714 Aromatic+heterocycle 1555-1520-1504-1480

STAGE 8: 4-((6-chloro-1,3-benzodioxol-5-yl) methyl)-1-cyclohexylmethyl)-3-(2-thienyl)-1H-pyrazole 5-carboxylic acid 2.8 ml of ethanol, 114.6 mg of the product obtained in Stage 7 above are introduced, 284 ul of soda (2 N) is added and the medium is taken to reflux for 2 hours. The ethanol is evaporated off, 15 ml of distilled $H_2O$ is added, followed by filtering, then neutralizing with 284 ul of hydrochloric acid (2 N). The suspension is left at ambient temperature overnight, for 10 minutes at 50° C., and for 5 minutes under ultrasound, followed by filtering, washing with water and drying. In this way 90.9 mg of expected product is obtained. M.p.=254° C. ANALYSES Microanalyses: $C_{23}H_{23}ClN_2O_4S$: MW 458.97

|  | Calculated | Found |
| --- | --- | --- |
| C% | 60.19 | 60.5 |
| H% | 5.05 | 5.2 |
| N% | 6.10 | 5.8 |
| S% | 6.99 | 6.7 |
| Cl% | 7.72 | 7.6 |

IR Spectrum: Nujol ($cm^{-1}$) Absorption OH/NH C=O 1686 Aromatic+heterocycle 1518-1500.

EXAMPLE 9

4-((6-chloro-1,3-benzodioxol-5-yl) methyl) 1-(cyclohexylmethyl)-3-(2-pyridinyl)-1H-pyrazole-5-carboxylic acid STAGE 1: ethyl 4-((6-chloro-1,3-benzodioxol-5-yl) methyl)-1-(cyclohexylmethyl)-3-(2-pyridinyl)-1H-pyrazole 5-carboxylate 10 ml of toluene (anhydrous), 368.4 mg of 2-(tributylstannyl)-pyridine and 29 mg of $Pd(Po_3)_4$ are introduced then 241.9 mg of the product obtained in Stage 6 of Example 8 is introduced rapidly, and the medium is taken to reflux overnight.

Ethyl acetate is added, the organic phase is washed with $H_2O$ saturated with ammonium chloride, with water then with water saturated with sodium chloride, dried, filtered and evaporated to dryness. After chromatography on silica eluting with ethyl acetate-methylene chloride: 10–90, 174.7 mg of expected product is obtained. ANALYSES IR Spectrum: in $CHCl_3$ $(cm^{-1})$ >=O 1710 Aromatic+heterocycle 1592-1568-1522-1504-1480.

STAGE 2: 4-((6-chloro-1,3-benzodioxol-5-yl) methyl)-1-(cyclohexylmethyl)-3-(2-pyridinyl)-1H-pyrazole-5-carboxylic acid 3.4 ml of ethanol, 164 mg of the product obtained in Stage 1 above, 340 ul of soda (2 N) are introduced and the medium is taken to 80° C. for 2 hours. Evaporation is carried out to eliminate the ethanol, 12 ml of distilled water is added, 340 ul of hydrochloric acid (2 N) is added, the suspension is left under agitation for 24 hours, then for 1 hour at 50° C. and for 30 minutes under ultrasound, followed by filtering, washing with water and drying. In this way 140.8 mg of expected product (white solid) is obtained. M.p.=238° C. ANALYSES Microanalyses: $C_{23}H_{24}ClN_3O_4$: MW 453.93

|     | Calculated | Found |
| --- | --- | --- |
| C%  | 63.50 | 63.2 |
| H%  | 5.33 | 5.2 |
| Cl% | 7.81 | 7.8 |
| N%  | 9.26 | 9.1 |

IR Spectrum: Nujol $(cm^{-1})$ Absorption OH/NH C=O 1688 Aromatic+heterocycle 1591-1568-1526-1500.

EXAMPLE 10

4-((6-chloro-1,3-benzodioxol-5-yl) methyl) 1-(cyclohexylmethyl)-3-(3-thienyl)-1H-pyrazole-5-carboxylic acid STAGE 1: ethyl 4-((6-chloro-1,3-benzodioxol-5-yl) methyl) 1-(cyclohexylmethyl) 3-(3-thienyl)-1H-pyrazole 5-carboxylate The operation is carried out as in Stage 7 of Example 8 starting with 5.0 ml of dimethylformamide (anhydrous), 96 mg of 3-thiophen-boronic acid, 17 mg of $Pd(Po_3)_4$ and 212.3 mg of $K_3PO_4$, 241.9 mg of the product obtained in Stage 6 of Example 8 and the reaction medium is taken to 100° C. for 16 hours. After chromatography on silica, eluting with methylene chloride-cyclohexane: 1-1, 197.5 mg of expected product is obtained. ANALYSES IR Spectrum: in $CHCl_3$ $(cm^{-1})$ >=O 1710 Aromatic+heterocycle 1600-1560-1524-1505-1480.

STAGE 2: 4-((6-chloro-1,3-benzodioxol-5-yl) methyl)-1-(cyclohexylmethyl)-3-(3-thienyl)-1H-pyrazole 5-carboxylic acid The operation is carried out as in Stage 8 of Example 8 starting with 3.94 ml of ethanol, 186.9 mg of the product obtained in Stage 1 above, 394 ul of soda (2 N) and the medium is then taken to reflux for 2 hours 30 minutes. In this way 165.3 mg of expected product (white solid) is obtained. M.p.=250° C. ANALYSES Microanalyses: $C_{23}H_{23}ClN_2O_4S$: MW 458.97

|     | Calculated | Found |
| --- | --- | --- |
| C%  | 60.19 | 60.3 |
| H%  | 5.05 | 5.0 |
| N%  | 6.10 | 5.9 |
| S%  | 6.99 | 6.9 |
| Cl% | 7.72 | 7.7 |

IR Spectrum: Nujol $(cm^{-1})$ Absorption OH/NH C=O 1683 Aromatic+heterocycle 1520-1500.

EXAMPLE 11

1-butyl 3-((4-(carboxymethyl) cyclohexyl) thio) 5-((6-chloro 1,3-benzodioxol-5-yl) methyl) 1H-pyrazole 4-carboxylic acid The operation is carried out as in Example 2 using in Stage 7 the crude mercaptan pyrazole obtained as in Stage 6 and terbutyl 4-bromocyclohexyl acetate and by maintaining agitation for 20 hours. The expected product is obtained. M.p.=100° C.

EXAMPLE 12

3-((5-carboxypentyl) thio) 5-((6-chloro 1,3-benzodioxol-5-yl) methyl) 1-propyl 1H-pyrazole 4-carboxylic acid Stage 1: ethyl 2-((6-chloro 1,3-benzodioxol-5-yl) methyl) 4-(methylthio) 1H-pyrazole 3-carboxylate 500 mg of the product obtained in Stage 3 of Example 2, 5 ml of ethanol and 0.12 ml of hydrazine hydrate are mixed together, agitation is carried out for 1 hour at ambient temperature, the solvent and the methylmercaptan vapours are eliminated and 357 mg of crude product is collected after chromatography on silica (eluant: $CH_2Cl_2$-AcOEt 8-2). M.p.=63° C.

Stage 2: ethyl 1-propyl 3-((6-chloro 1,3-benzodioxol-5-yl) methyl) 5-(methylthio) 1H-pyrazole 4-carboxylate (A) ethyl 1-propyl 2-((6-chloro 1,3-benzodioxol-5-yl) methyl) 4-methylthio) 1H-pyrazole 3-carboxylate (B)

12.85 g of the product obtained as in Stage 1 above, 200 ml of dimethylformamide and 1.74 g of sodium hydride are mixed together. Agitation is carried out for 15 minutes at ambient temperature, 8.15 ml of bromopropane is added, agitation is carried out for 16 hours, the whole is poured into water, extraction is carried out with ethyl acetate, the solvent is eliminated under reduced pressure, the residue is chromatographed on silica (eluant: cyclohexane-ether 8-2) and 2.03 g of expected product, isomer A M.p.=50° C. and 8.66 g of expected product, isomer B M.p.=94° C. are obtained.

Stage 3: ethyl 1-propyl 5-((6-chloro 1,3-benzodioxol-5-yl) methyl) 3-(methylsulphinyl) 1H-pyrazole 4-carboxylate The operation is carried out as in Stage 5 of Example 2 using at the start 8.66 g of the product obtained in Stage 2 above and 6.46 g of metachloroperbenzoic acid. 7.39 g of expected product is obtained which is used as it is for the following stage.

Stage 4: ethyl 1-propyl 5-((6-chloro 1,3-benzodioxol-5-yl) methyl) 3-mercapto 1H-pyrazole 4-carboxylate The operation is carried out as in Stage 6 of Example 2 using at the start 4.25 g of the product obtained in Stage 3 above. 4.2 g of expected product is obtained.

Stage 5: ethyl 1-propyl 5-((6-chloro 1,3-benzodioxol-5-yl) methyl) 3-((6-ethoxycarbonylpentyl) thio) 1H-pyrazole 4-carboxylate The operation is carried out as in Stage 7 of Example 2 using at the start 685 mg of the product obtained in Stage 4 above and 0.96 ml of ethyl 6-bromo hexanoate and maintaining agitation for 20 hours. 250 mg of expected product is obtained.

Stage 6: 3-((5-carboxypentyl) thio) 5-((6-chloro 1,3-benzodioxol-5-yl) methyl) 1-propyl 1H-pyrazole 4-carboxylic acid The operation is carried out as in Stage 8 of Example 2 using at the start 250 mg of the diester prepared in Stage 5 above. 137 mg of expected product is obtained. M.p.=88° C.

EXAMPLE 13

3-((4-(carboxymethyl) cyclohexyl) thio) 5-((6-chloro 1,3-benzodioxol-5-yl) methyl) 1-propyl 1H-pyrazole 4-carboxylic acid The operation is carried out as in Example 12 by reacting, in Stage 5, terbutyl 4-bromocyclohexyl ethylate on ethyl 1-propyl 5-((6-chloro 1,3-benzodioxol-5-yl) methyl) 3-mercapto 1H-pyrazole 4-carboxylate. The expected product is obtained. M.p.=178° C.

EXAMPLE 14 ethyl 3-((3-carboxypropyl) thio) 5-((6-chloro 1,3-benzodioxol-5-yl) methyl) 1-propyl 1H-pyrazole 4-carboxylate The operation is carried out as in Example 12 by reacting, in Stage 5, ethyl 4-bromobutyrate on ethyl 1-propyl 5-((6-chloro 1,3-benzodioxol-5-yl) methyl) 3-mercapto 1H-pyrazole 4-carboxylate. The expected product is obtained. M.p.=110° C.

EXAMPLE 15

3-((4-carboxybutyl) thio) 5-((6-chloro 1,3-benzodioxol-5-yl) methyl) 1-propyl 1H-pyrazole 4-carboxylic acid The operation is carried out as in Example 12 by reacting, in Stage 5, ethyl 5-bromo valerate on ethyl 1-propyl 5-((6-chloro 1,3-benzodioxol-5-yl) methyl) 3-mercapto 1H-pyrazole 4-carboxylate. The expected product is obtained. M.p.=185° C.

EXAMPLE 16

3-((6-carboxyhexyl) thio) 5-((6-chloro 1,3-benzodioxol-5-yl) methyl) 1-propyl 1H-pyrazole 4-carboxylic acid The operation is carried out as in Example 12 by reacting, in Stage 5, ethyl 7-bromo heptanoate on ethyl 1-propyl 5-((6-chloro 1,3-benzodioxol-5-yl) methyl) 3-mercapto 1H-pyrazole 4-carboxylate. The expected product is obtained. M.p.=180° C.

EXAMPLE 17

1-((4-(carboxymethyl) phenyl) methyl) 4-((6-chloro 1,3-benzodioxol-5-yl) methyl) 3-phenyl 1H-pyrazole 5-carboxylic acid Stage A: ethyl 1-(((4-ethoxycarbonylmethyl) phenyl) methyl) 4-((6-chloro 1,3-benzodioxol-5-yl) methyl) 3-phenyl 1H-pyrazole 5-carboxylate and corresponding 5-phenyl isomer 1) Preparation of the Halogenated Ester 2.44 ml of trimethylsilyl chloride is slowly added to 2 g of 4-bromo methyl phenyl acetic acid in 40 ml of ethanol and agitation is carried out for 2 hours at ambient temperature. The solvent is evaporated off, the residue is taken up in dichloromethane, washed with water, dried and evaporated to dryness under reduced pressure. 1.98 g of expected product is obtained. M.p.<45° C.

2) Coupling 40 mg of sodium hydride at 50% is added to 300 mg of the ester obtained as in Stage 2 of Example 1 in 3 cm³ of dimethylformamide. Agitation is carried out for 15 minutes then 218 mg of the halogenated ester obtained previously is added. After agitation for 3 hours at ambient temperature, the reaction medium is poured into water, extracted with ethyl acetate and the solvent is evaporated off under reduced pressure. The residue is chromatographed on silica (eluant: $CH_2Cl_2$-AcOEt 98-2) and 206 mg of expected product is obtained in the form of the 3-phenyl isomer (M.p. #90° C.) and 92 mg is obtained in the form of the 5-phenyl isomer.

Stage B: 1-((4-(carboxymethyl) phenyl) methyl) 4-((6-chloro 1,3-benzodioxol-5-yl) methyl) 3-phenyl 1H-pyrazole 5-carboxylic acid By operating as in Example 1 Stage 4 starting with 186 mg of the 3-phenyl isomer obtained in Stage A above, 154 mg of expected product was obtained. M.p.=250° C.

EXAMPLE 18

1-((4-carboxycyclohexyl) methyl) 4-((6-chloro 1,3-benzodioxol-5-yl) methyl) 3-phenyl 1H-pyrazole 5-carboxylic acid The operation is carried out as in Example 17, using ethyl 1-((4-tosyloxymethyl) cyclohexyl) carboxylate instead of the halogenated ester and the expected product is obtained.
Preparation of the Tosylate 1 g of 1,4-dihydroxymethyl cyclohexane in 10 ml of dimethylformamide is agitated for 5 hours at ambient temperature in the presence of 0.94 g of imidazole and 1.8 ml of diphenyl trimethyl silane chloride then the whole is poured into a saturated aqueous solution of ammonium chloride, followed by extraction with ethyl acetate, washing with salt water and drying, the solvent is evaporated off under reduced pressure, the residue is chromatographed on silica (eluant: $CH_2Cl_2$-AcOEt 95-5). 1.31 g of the silylated derivative is obtained. 13.06 g of the silylated derivative prepared as indicated above in 260 ml of dimethylformamide with 45 g of pyridinium dichromate is agitated at ambient temperature for 40 hours, followed by partial concentration under reduced pressure, the whole is poured into 400 ml of ice-cooled hydrochloric acid (N), extracted with ethyl acetate, washed with a sodium bicarbonate solution and dried, the solvent is evaporated off under reduced pressure, 13.1 g of crude acid is obtained. 12.53 g of the acid obtained above in 125 ml of 100° ethanol is agitated for 70 hours at ambient temperature in the presence of 10 ml of chlorotrimethylsilane then the solvents are evaporated off under reduced pressure. After chromatography on silica (eluant $CH_2Cl_2$-AcOEt 95-5 to 80-20), 3.40 g of the unblocked ester is obtained.
Formation of the Tosylate 3.40 g of the preceding derivative in 10 ml of pyridine is cooled down to 0°/+5° C., 5.22 g of tosyl chloride in 25 ml of dichloromethane is added over 50 minutes and agitation is carried out for 20 hours at ambient temperature. The reaction medium is poured into 200 ml of N hydrochloric acid, followed by extraction with dichloromethane, washing with water and drying, the solvent is evaporated off under reduced pressure, the residue is chromatographed on silica (eluant: cyclohexane/AcOEt 2-8) and 5.50 g of expected tosylate is obtained.

EXAMPLE 19

(cis/trans) 1-((4-(carboxymethyl) cyclohexyl) methyl) 4-((6-chloro 1,3-benzodioxol-5-yl) methyl) 3-phenyl 1H-pyrazole 5-carboxylic acid By operating as in Example 17 using the tosylate prepared below instead of the halide, the expected product is obtained.
Preparation of 1-cyanomethyl 4-tosyloxymethyl cyclohexane used at the start of Example 19
1) Formation of the Ditosylate 10 g of 1,4-cyclohexane dimethanol in 50 ml of pyridine is cooled down to 0°/+5° C., 32 g of tosyl chloride in 150 ml of dichloromethane is added over 1 hour then agitation is carried out at ambient temperature for 48 hours. The reaction medium is poured into 500 ml of 2 N hydrochloric acid, followed by extraction with dichloromethane, the extracts are washed with water and dried, the solvent is evaporated off under reduced pressure. After recrystallization of the residue from a mixture of dichloromethane/ethyl acetate, 16.28 g of expected product is obtained. M.p.=165° C.

2) Preparation of Cyanated Product 4.52 g of the tosylate prepared above in 90 ml of dimethylformamide is agitated for 3 days at ambient temperature in the presence of 490 mg of sodium cyanide. The reaction medium is poured into water to which sodium bicarbonated has been added, followed by extraction with ethyl acetate, the extracts are washed with water and dried, the solvent is evaporated off under reduced pressure. After chromatography on silica (eluant: cyclohexane-$CH_2Cl_2$-AcOEt 5-4-1), 1.4 g of expected reagent is obtained. M.p. #75° C.

EXAMPLE 20

1-((bicyclo (2.2.2) oct-2-yl) methyl 4-((6-chloro 1, 3-benzodioxol-5-yl) methyl) 3-phenyl 1H-pyrazole 5-carboxylic acid By operating as in Example 17 using 1-tosyloxymethyl bicyclo(2.2.2)octane instead of the halogenated ester, the expected product is obtained. M.p.=120° C.

EXAMPLE 21

1-((4-(carboxycyclohexyl) methyl) 4-((6-chloro 1,3-benzodioxol-5-yl) methyl) 3-(2-thienyl) 1H-pyrazole 5-carboxylic acid Stage A: ethyl α,γ-dioxo 2-thiophènebutanoate 20 g of sodium ethylate in 600 ml of ethanol is cooled down to 0° C. then 15 ml of 2-acetyl thiophene is added slowly, agitation is carried out for 2 hours at 0° C., 28 ml of diethyl oxalate is added over 25 minutes, the reaction medium is left to return to ambient temperature, agitation is carried out for 20 hours, the whole is cooled down again to 0° C. then hydrolyzed by the addition of 500 ml of hydrochloric acid (N). After returning to ambient temperature, the ethanol is evaporated off under reduced pressure, extraction is carried out with ethyl acetate, the extracts are washed with salt water and dried, the solvent is evaporated off under reduced pressure, 31.3 g of expected product is obtained after chromatography on silica (eluant: $CH_2Cl_2$-AcOEt 100% to 50%). M.p.<37° C.

Stage B: ethyl β-((6-chloro 1,3-benzodioxol-5-yl) méthyl)-α,γ-dioxo-2-thiophènebutanoate 10 g of sodium ethylate is added to 31.11 g of the product obtained in Stage A in 155 ml of dimethylformamide, agitation is carried out for 15 minutes, then 28.2 g of 6-chloropiperonyl chloride and 20.6 g of sodium iodide are added. After agitation for 17 hours at ambient temperature, the reaction medium is poured into water and extracted with ethyl acetate, the solvent is eliminated under reduced pressure.

Stage C: ethyl 4-((6-chloro 1,3-benzodioxol-5-yl) methyl) 3-(2-thienyl) 1H-pyrazole 5-carboxylate 53.23 g of the crude product obtained above in 100 ml of ethanol is heated to 80° C. and 7 ml of hydrazine hydrate is added and agitation is carried out for 3 hours under reflux, the reaction medium is left to return to ambient temperature, the precipitate is filtered off, washed with ethanol, dried under reduced pressure, taken up in ethanol under reflux, concentrated under reduced pressure and 7.97 g of expected crystallized product is collected.

Stage D: ethyl 1-(((4-(ethoxycarbonyl) cyclohexyl) methyl) 4-((6-chloro 1,3-benzodioxol-5-yl) methyl) 3-(2-thienyl) 1H-pyrazole 5-carboxylate 700 mg of the product obtained in Stage C above in 4.2 ml of dimethylformamide is agitated for 15 minutes in the presence of 112 mg of sodium hydride at 50%. 730 mg of ethyl 1-((4-tosyloxymethyl) cyclohexyl) carboxylate prepared as in Example 18 in 2 ml of dimethylformamide is added at ambient temperature, agitation is carried out for 66 hours, another 305 mg of this tosylate in 1 ml of dimethylformamide is added, the reaction medium is heated for 3 hours at 80° C., left to return to ambient temperature, poured into a saturated aqueous solution of ammonium chloride, extraction is carried out with ethyl acetate, followed by drying, the solvents are evaporated off under reduced pressure, the residue is chromatographed on silica (eluant: cyclohexane-ethyl acetate 9-1 and 8-2 then $CH_2Cl_2$-AcOEt 99-1) and after crystallization from ether 467 mg of expected product is obtained.

Stage E: 1-((4-(carboxycyclohexyl) methyl) 4-((6-chloro 1,3-benzodioxol-5-yl) methyl) 3-(2-thienyl) 1H-pyrazole 5-carboxylic acid The operation is carried out as in Stage 8 of Example 2 using 245 mg of the diester prepared above and 0.88 ml of 2 N soda. 124 mg of expected product is obtained. M.p.=285° C. (decomp).

EXAMPLE 22 cis/trans 1-((4-(carboxymethyl) cyclohexyl) methyl) 4-((6-chloro 1,3-benzodioxol-5-yl) methyl) 3-(2-thienyl) 1H-pyrazole 5-carboxylic acid The operation is carried out as in Example 21 Stages D and E using 1-cyanomethyl 4-tosyloxymethyl cyclohexane prepared as in Example 19 as the tosylated reagent, and by carrying out the reaction at ambient temperature for 16 hours. The expected product is obtained. M.p.=240° C.

EXAMPLE 23

1-((2-(carboxymethoxy) phenyl) methyl) 4-((6-chloro 1,3-benzodioxol-5-yl) methyl) 3-(2-thienyl) 1H-pyrazole 5-carboxylic acid The operation is carried out as in Example 21 Stages D and E using 2-((ethoxycarbonylmethoxy) benzyl) chloride in instead of the tosylated reagent. The expected product is obtained. M.p.>260° C.

EXAMPLE 24

1- ((3-carboxycyclohexyl) methyl) 4-((6-chloro 1,3-benzodioxol-5-yl) methyl) 3-(2-thienyl) 1H-pyrazole 5-carboxylic acid The operation is carried out as in Example 21 Stages D and E using ethyl 1-((3-tosyloxymethyl) cyclohexyl) carboxylate prepared as indicated in Example 5 as the tosylated reagent and carrying out the reaction at ambient temperature. The expected product is obtained. M.p.>260° C.

EXAMPLE 25

1-(2-carboxymethoxy) 4-methoxyphenyl) 4-((6-chloro 1,3-benzodioxol-5-yl) methyl) 3-(2-thienyl 1H-pyrazole 5-carboxylic acid The operation is carried out as in Example 21 Stages D and E using 4-methoxy 2-((ethoxycarbonylmethoxy)

benzyl) chloride instead of the tosylated reagent. The expected product is obtained. M.p.=260° C.

EXAMPLE 26

4-((6-chloro 1,3-benzodioxol-5-yl) methyl) 1-(cyclohexylmethyl) 3-(3-pyridinyl) 1H-pyrazole 5-carboxylic acid Stage A: ethyl 4-((6-chloro 1,3-benzodioxol-5-yl) methyl) 1-(cyclohexylmethyl) 3-(3-pyridinyl) 1H-pyrazole 5-carboxylate 254 mg of the brominated derivative prepared as indicated in Stage 6 of Example 8, in 10 ml of toluene is added under an inert atmosphere to a mixture containing 386 mg of 3-(tributylstannyl) pyridine and 30 mg of tetrakistriphenylphoshine palladium. The reaction medium is heated for 18 hours under reflux, another 30 mg of palladium-containing reagent is added, the whole is maintained under reflux for 4 hours and 30 minutes then it is poured into 50 ml of water. Extraction is carried out with dichloromethane, followed by washing with water and drying, the solvent is evaporated off under reduced pressure, the residue is chromatographed on silica (eluant: cyclohexane-AcOEt 7-3) and after recrystallization from an ether-isopropyl ether mixture, 144 mg of expected product is obtained. M.p.=135° C.

Stage B: 4-((6-chloro 1,3-benzodioxol-5-yl) methyl) 1-(cyclohexylmethyl) 3-(3-pyridinyl) 1H-pyrazole 5-carboxylic acid The operation is carried out as in Stage 4 of Example 1 using 130 mg of the ester obtained in Stage A and 0.27 ml of 2 N soda. 98 mg of expected product is collected. M.p.=144° C.

EXAMPLE 27

4-((6-chloro 1,3-benzodioxol-5-yl) methyl) 1-(cyclohexylmethyl) 3-(2-furanyl) 1H-pyrazole 5-carboxylic acid The operation is carried out as in Example 26 Stages A and B using 700 mg of brominated derivative and 0.70 ml of 2-(tributylstannyl) furan in Stage A. 436 mg of ester is obtained. 404 mg of this ester and 0.86 ml of 2 N soda are reacted and 339 mg of expected product is obtained. M.p.=248° C.

EXAMPLE 28

1-((4-carboxycyclohexyl) methyl) 4-((6-chloro 1,3-benzodioxol-5-yl) methyl) 3-(2-pyridinyl) 1H-pyrazole 5 -carboxylic acid Stage A: ethyl α,γ-dioxo 2-pyridinebutanoate 3 g of sodium ethylate in 120 ml of ethanol is cooled down to 0° C., 6 ml of 2-acetyl pyridine is added, agitation is carried out for 5 minutes at 0° C. then 12 ml of diethyloxalate is added over 5 minutes. The reaction medium is maintained under agitation at 0° C. for 1 hour, left to return to ambient temperature over 2 hours and 30 minutes, the solvent is evaporated off under reduced pressure, the residue is taken up in ether, filtered and dried under reduced pressure at 70° C. 8.84 g of expected product is obtained. M.p.=155° C.

Stage B: ethyl β-((6-chloro 1,3-benzodioxol-5-yl) α,γ-dioxo 2-pyridinebutanoate 7.71 g of the product obtained in the preceding stage is mixed with 20 ml of dimethylformamide then 6.45 g of 6-piperonyl chloride and 7 g of sodium iodide in 40 ml of dimethylformamide are added. Agitation is carried out for 4 hours and 30 minutes, the reaction medium is poured into water, extracted with dichloromethane, the extracts are washed with water and dried, the solvent is evaporated off under reduced pressure and the expected product is obtained which is used as it is for the following stage.

Stage C: ethyl 4-((6-chloro 1,3-benzodioxol-5-yl) methyl) 3-(2-pyridinyl) 1H-pyrazole 5-carboxylate The operation is carried out as in Example 21 Stage C using 12.58 g of the product obtained in Stage B and 1.2 ml of hydrazine hydrate and 4.98 g of expected product is obtained.

Stage D: ethyl 1-(((4-ethoxycarbonyl) cyclohexyl) methyl) 4-((6-chloro 1,3-benzodioxol-5-yl) methyl) 3-(2-pyridinyl) 1H-pyrazole 5-carboxylate The operation is carried out as in Example 21 Stage D using 638 mg of the product obtained in Stage C and 700 mg of ethyl 1-((4-tosyloxymethyl) cyclohexyl) carboxylate prepared as in Example 18. 456 mg of expected product is obtained.

Stage E: 1-((4-carboxycyclohexyl) methyl) 4-((6-chloro 1,3-benzodioxol-5-yl) methyl) 3-(2-pyridinyl) 1H-pyrazole 5 -carboxylic acid The operation is carried out as in Stage 8 of Example 2 using 423 mg of the diester prepared above and 1.53 ml of 2 N soda. 262 mg of expected product is obtained. M.p.=261° C.

EXAMPLE 29

Pharmaceutical Composition

Tablets were prepared corresponding to the following formula:

Product of Example 8 . . . 50 mg

Excipient for a tablet made up to . . . 200 mg (detail of excipient: lactose, talc, starch, magnesium stearate).

PHARMACOLOGICAL RESULTS

1) STUDY OF THE ACTIVITY ON THE ENDOTHELIN A RECEPTOR

A membrane preparation is prepared from the heart (ventricles) of a rat. The tissue is ground up in a POLYTRON in a 50 mM Tris buffer pH=7.4.

After 30 minutes at 25° C. (W.B.) the homogenate is centrifuged at 30,000 g for 15 minutes (2 centrifugations with intermediate take-up in the Tris buffer pH 7.4).

The pellets are suspended in an incubation buffer (25 mM Tris, 5 microg/ml pepstatin A, 3 microg/ml aprotinin, 0.1 mm PMSF, 3 mM EDTA, 1 mM EGTA pH 7.4).

2 ml aliquoted fractions are distributed in hemolysis tubes and $^{125}$I endothelin (approx. 5,000 dpm/tube) and the product to be studied are added. (The product is first tested at $3\times10^{-5}$ M three times). When the tested product displaces more than 50% of the radioactivity specifically bound to the receptor, it is tested again according to a range of 7 concentrations in order to determine the concentration which inhibits by 50% the radioactivity specifically bound to the receptor. In this way the 50% inhibitory concentration is determined.

The non-specific bond is determined by the addition of endothelin at $10^{-6}$ M (three times). After incubation at 25° C. for 60 minutes, replacing in a water bath at 0° C. for 5 minutes, filtration under reduced pressure and rinsing with Tris buffer pH 7.4, the radioactivity is counted in the presence of scintillating Triton.

The result is expressed directly as the 50% inhibitory concentration ($IC_{50}$), that is to say as the concentration of product studied, expressed in nM, necessary to displace 50% of the specific radioactivity fixed to the receptor studied.

Result

The IC$_{50}$'s found for the products of the examples are given in Table 1 hereafter, in nanomoles.

Results

TABLE I

| Product of examples | Endothelin A receptor IC$_{50}$ in nanomoles |
|---|---|
| 1 | 3, 6 |
| 5 | 2, 5 |
| 8 | 1, 1 |
| 9 | 4, 7 |
| 10 | 1, 1 |

1) STUDY OF THE ACTIVITY ON THE ENDOTHELIN B RECEPTOR

A membrane preparation is prepared from the rear cortex plus the cerebellum of a rat. The tissue is ground up in a POLYTRON in a 50 mM Tris buffer pH=7.4.

After 30 minutes at 25° C. (W.B.) the homogenate is centrifuged at 30,000 g for 15 minutes (2 centrifugations with intermediate take-up in the Tris buffer pH 7.4).

The pellets are suspended in an incubation buffer (25 mM Tris, 5 microg/ml pepstatin A, 3 microg/ml aprotinin, 0.1 mM PMSF, 3 mM EDTA, 1 mM EGTA pH 7.4).

2 ml aliquoted fractions are distributed in hemolysis tubes and $^{125}$I endothelin (approx. 5,000 dpm/tube) and the product to be studied are added. (The product is first tested at $3\times10^{-5}$ M three times). When the tested product displaces more than 50% of the radioactivity specifically bound to the receptor, it is tested again according to a range of 7 concentrations in order to determine the concentration which inhibits by 50% the radioactivity specifically bound to the receptor. In this way the 50% inhibitory concentration is determined.

The non-specific bond is determined by the addition of endothelin at $10^{-6}$ M (three times). After incubation at 25° C. for 60 minutes, replacing in a water bath at 0° C. for 5 minutes, filtration under reduced pressure and rinsing with Tris buffer pH 7.4, the radioactivity is counted in the presence of scintillating Triton.

The result is expressed directly as the 50% inhibitory concentration (IC$_{50}$), that is to say as the concentration of product studied, expressed in nM, necessary to displace 50% of the specific radioactivity fixed to the receptor studied.

Result

The IC$_{50}$'s found for the products of the examples are given in Table 2 hereafter, in nanomoles.

Results

TABLE II

| Product of examples | Endothelin A receptor IC$_{50}$ in nanomoles |
|---|---|
| 1 | 2, 6 |
| 5 | 14, 8 |
| 8 | 1, 7 |
| 9 | 3, 4 |
| 10 | 3, 2 |

We claim:

1. A compound selected from the group consisting of a compound of the formula

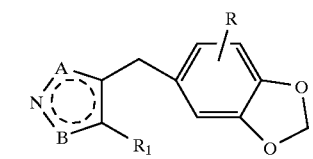

in which one of A and is nitrogen and the other of A and B is methine, defined as follows:

A is either a nitrogen atom substituted alkyl or alkenyl of up to 10 carbon atoms, or methine substituted by CA which is saturated or unsaturated cycloalkyl of 3 to 7 members, and optionally containing at least one heteroatom selected from the group consisting of oxygen, sulphur and nitrogen, B is either a nitrogen substituted by ZNB which is alkyl or alkenyl of up to 10 carbon atoms, optionally substituted by cycloalkyl of 5 or 6 members itself optionally substituted by a member selected from the group consisting of carboxyalkoxyalkyl of up to 6 carbon atoms, or a methine substituted by CB which is selected from the group consisting of alkyl, alkenyl or alkylthio of up to carbon atoms, and cycloalkylthio of 5 or 6 members, all optionally substituted by carboxy or phenyl unsubstituted or substituted by a member selected from the group consisting of free or esterified carboxy alkyl and alkoxy of 1 to 4 carbon atoms, R is selected from the group consisting of hydrogen halogen and alkoxy of 1 to 4 carbon atoms, R$_1$ is free, salified or esterified carboxy or an acid ester, the dotted lines indicate that the ring which carries A and B is unsaturated, the compounds being in all possible racemic, enantiomeric and diastereoisomeric isomer forms, as well as the addition salts with mineral and organic acids.

2. A compound of claim 1 wherein

A is either a nitrogen substituted by alkyl of 1 to 4 carbon atoms, or a methine substituted by phenyl, thienyl or pyridyl, B is either a nitrogen substituted by alkyl of 1 to 4 carbon atoms substituted by a cyclohexyl unsubstituted or substituted by a carboxy radical or by a carboxymethoxymethyl, or a methine substituted by an alkylthio of 1 to 6 carbon atoms or by a cyclohexylthio, these unsubstituted by a carboxy or by a phenyl substituted by an alkoxy of 1 to 6 carbon atoms, with the proviso that when one of A and B is nitrogen, one of A and B is methine, substituted as indicated above, R$_1$ is free or esterified carboxy and R is halogen.

3. A compound of claim 1 wherein A is methine substituted by phenyl, thienyl or pyridyl, B is nitrogen substituted by a cyclohexylmethyl optionally substituted by a carboxy or carboxymethyl in which the carboxy is free or esterified, R$_1$ is free, esterified or salified carboxy or a free or salified tetrazolyl and R is hydrogen or halogen.

4. A compound of claim 1 selected from the group consisting of 4-((6-chloro-1,3-benzodioxol-5-yl) methyl)-1-(cyclohexylmethyl) 3-phenyl 1H-pyrazole 5-carboxylic acid, and 1-butyl-5-((6-chloro-1,3-benzodioxol-5-yl) methyl)-3-((5-carboxypentyl)thio)-1H-pyrazole-4-carboxylic acid, 1-((3-carboxycyclohexyl) methyl)-4-((6-chloro 1,3-benzodioxol-5-yl) methyl) 3-phenyl-1H-pyrazole-5-carboxylic acid, 4-((6-chloro-1,3-benzodioxol-5-yl) methyl)-1-(cyclohexylmethyl) 3-(2-thienyl)-1H-pyrazole 5-carboxylic acid, 4-((6-chloro-1,3-benzodioxol-5-yl) methyl)-1-(cyclohexylmethyl) 3-(2-pyridinyl)-1H-pyrazole-5-carboxylic acid, 4-((6-chloro-1,3-benzodioxol-5-yl) methyl)-1-(cyclohexylmethyl) 3-(3-thienyl)-1H-pyrazole-5-carboxylic acid, 1-butyl 3-((4-(carboxymethyl) cyclohexyl) thio) 5-((6-chloro 1,3-benzodioxol-5-yl) methyl) 1H-pyrazole 4-carboxylic acid, 3-((4-(carboxymethyl) cyclohexyl) thio) 5-((6-chloro 1,3-benzodioxol-5-yl) methyl) 1-propyl 1H-pyrazole 4-carboxylic acid, 1-((bicyclo(2.2.2)oct-2-yl) methyl) 4-((6-chloro 1,3-benzodioxol-5-yl) methyl) 3-phenyl 1H-pyrazole 5-carboxylic acid, 1-((4-carboxycyclohexyl) methyl) 4-((6-chloro 1,3-benzodioxol-5-yl) methyl) 3-(2-thienyl) 1H-pyrazole 5-carboxylic acid, cis/trans 1-((4-(carboxymethyl) cyclohexyl) methyl) 4-((6-chloro 1,3-benzodioxol-5-yl) methyl) 3-(2-thienyl) 1H-pyrazole 5-carboxylic acid, 1-((2-(carboxymethoxy) phenyl) methyl) 4-((6-chloro 1,3-benzodioxol-5-yl) methyl) 3-(2-thienyl) 1H-pyrazole 5-carboxylic acid, 1-((3-carboxycyclohexyl) methyl) 4-((6-chloro 1,3-benzodioxol-5-yl) methyl) 3-(2-thienyl) 1H-pyrazole 5-carboxylic acid.

5. A method for treating illnesses due to an abnormal stimulation of endothelial receptors in warm-blooded animals comprising administering to warm-blooded animals an effective amount of a compound of claim 1 sufficient to treat illness resulting from an abnormal stimulation of endothelial receptors.

6. A compound of claim 1 wherein $R_1$ is selected from the group consisting of carboxy, carboxy esterified with an alkanol of 1 to 6 carbon atoms, tetrazolyl and esterified tetrazolyl.

* * * * *